(12) United States Patent
Crosset

(10) Patent No.: US 11,266,139 B2
(45) Date of Patent: Mar. 8, 2022

(54) OVEN FOR CONTINUOUS ELIMINATION OF PHYTOSANITARY PESTS PRESENT IN ORGANIC PARTICLES OF PLANT ORIGIN

(71) Applicant: Léon Crosset, Thimister-Clermont (BE)

(72) Inventor: Léon Crosset, Thimister-Clermont (BE)

( * ) Notice: Subject to any disclaimer, the term of this patent is extended or adjusted under 35 U.S.C. 154(b) by 336 days.

(21) Appl. No.: 16/464,548

(22) PCT Filed: Nov. 27, 2017

(86) PCT No.: PCT/EP2017/080493
§ 371 (c)(1),
(2) Date: May 28, 2019

(87) PCT Pub. No.: WO2018/099850
PCT Pub. Date: Jun. 7, 2018

(65) Prior Publication Data
US 2021/0105992 A1    Apr. 15, 2021

(30) Foreign Application Priority Data

Nov. 29, 2016  (BE) .................................. 2016/5886

(51) Int. Cl.
*A01M 1/20* (2006.01)
*F27B 9/14* (2006.01)
(Continued)

(52) U.S. Cl.
CPC .............. *A01M 1/2094* (2013.01); *F27B 9/14* (2013.01); *F27B 9/3005* (2013.01); *F27B 9/40* (2013.01); *F27D 2003/0066* (2013.01)

(58) Field of Classification Search
CPC ....... A01M 1/2094; F27B 9/3005; F27B 9/14; F27B 9/40; F27D 2003/0066; A61L 2202/15; A61L 2/06
See application file for complete search history.

(56) References Cited

U.S. PATENT DOCUMENTS 3,958,920 A * 5/1976 Anderson ............... F27B 9/185
432/23
2011/0119948 A1* 5/2011 Niemann ............. F26B 17/005
34/209

FOREIGN PATENT DOCUMENTS

BE    1020153 A5    5/2013
BE    1024440 B1 *  2/2018 ............... A61L 2/06
(Continued)

OTHER PUBLICATIONS

Food and Agriculture Organization of the United Nations, International Plant Protection Convention, "International Standard for Phytosanitary Measures 15 (ISPM 15), Regulation of wood packaging material in international trade", Produced by the Secretariat of the International Plant Protection Convention (IPPC), Adopted 2013; Published 2016, 22 pages, ©FAO 2013; https://www.ippc.int/static/media/files/publication/en/2016/06/ISPM_15_2013_En_2016-06-07.pdf.

*Primary Examiner* — Steven S Anderson, II
(74) *Attorney, Agent, or Firm* — Blue Filament Law PLLC

(57) ABSTRACT

An oven for elimination of harmful organisms which pose phytosanitary risks and are present in material of plant origin in the form of particles is provided. The oven includes: (a) first and second circular plates mounted in rotation about an axis Z, the surface of said plates being perforated and permeable to air and water, (b) a means for transferring the collected particles from the first plate to the second plate, and (c) a gas-blowing means forming a closed gas cycle. The gas-blowing means includes a blower for accelerating a flow of gas and directing it towards a heating station in order to heat the gas and directing it parallel to the axis Z towards the first plate, passing through the perforated surface of the first plate, then directly afterwards through the perforated surface (Continued)

of the second plate, in order to return to the blower and recommence the gas cycle.

17 Claims, 4 Drawing Sheets

(51) Int. Cl.
*F27B 9/40* (2006.01)
*F27B 9/30* (2006.01)
*F27D 3/00* (2006.01)

(56) References Cited

FOREIGN PATENT DOCUMENTS

| | | | | | |
|---|---|---|---|---|---|
| EP | 0197171 | A1 | 10/1986 | | |
| EP | 1224946 | A1 | 7/2002 | | |
| GB | 449442 | A | * | 6/1936 | ............ F26B 17/005 |
| WO | 2013139720 | A1 | 9/2013 | | |

* cited by examiner

OVEN FOR CONTINUOUS ELIMINATION OF PHYTOSANITARY PESTS PRESENT IN ORGANIC PARTICLES OF PLANT ORIGIN

FIELD OF THE INVENTION

The invention relates to an oven making it possible to eliminate harmful organisms presenting phytosanitary risks, such as insects or other organisms present in particles, such as woodchips or sawdust. In particular, the present oven fulfills the phytosanitary requirements that apply generally to the importing of sawdust or woodchips and of bark, and other byproducts of wood in the form of particles, as well as dry cones intended for import to Europe or export from Europe. The present oven makes it possible to treat such materials continuously and effectively from an energy point of view.

TECHNOLOGICAL BACKGROUND

In a globalized commerce environment, the transportation of materials of plant origin through borders, in particular of wood in all its forms, generates a risk of dissemination of harmful organisms present in said materials. This risk relates for example to wood packaging and pallets, but it relates also to wood or other organic materials of plant origin in the form of particles, such as sawdust, chips, pellets, wood wool, pieces of bark, cones, etc.

In order to provide an effective defense against the risk of dissemination of the harmful organisms, while minimizing the risks of impeding international exchanges, international standards have been instituted that impose an insecticidal treatment on wood circulating between different countries. For example, increasing numbers of countries are applying the international standard for phytosanitary measures No. 15 from the United Nations Food and Agriculture Organization (FAO) concerning the "Guidelines for Regulating Wood Packaging Material in International Trade" (ISMP 15) to avoid the dissemination of wood parasites. The importing of goods into these countries has to be done with wood packaging (crates, pallets, etc.) which have been subjected to a strict phytosanitary treatment. In particular, the standard requires the packaging wood to be treated according to a heat treatment heating wood to a minimum central temperature of 56° C. for at least 30 minutes.

Although the ISMP 15 standard is valid only for block wood, an identical heat treatment is also required for imports of wood particles and other particles of plant origin by many countries.

A heat treatment raising the core of the particles to a treatment temperature, $T_t$, for example, of 56° C. and maintaining it for a time, $t_1$, for example, of 30 minutes, represents a technical and economical challenge for the exporter. Such a heat treatment may obviously be applied by batch, by treating a given volume of particles of plant origin in an oven or furnace of suitable capacity. However, such a method is lengthy and requires many manipulations to load the material to be treated in the oven; wait for it to reach the temperature, $T_t$; keep the material at the temperature, $T_t$, for a time, $t_1$; and unload the treated material from the oven. At the end of this method, a new volume of material to be treated can be reloaded and the cycle described above reproduced. Such a solution is unsatisfactory.

There are particle driers that operate continuously, such as, for example, the drier described in WO 2013139720 A1, which makes it possible to dry particles in highly advantageous time and energy conditions. However, drying particles consists in eliminating the water soaked in the particles, which does not have much to do with a heat treatment bringing the same particles to a temperature, $T_t$, and maintaining them at this temperature for a time, $t_1$. The use of a continuous drier is therefore not ideal for the phytosanitary treatment of wood particles and of other materials of plant origin.

The present invention proposes an oven that is particularly suited to the continuous treatment of wood particles and of other materials of plant origin satisfying the standards generally applied to exports of such products. The oven of the present invention makes it possible to ensure a temperature, $T_t$, and a time, $t_1$, of treatment of the particles in a method that is time-efficient, optimized in terms of energy and that occupies only a limited footprint. The oven of the present invention is easier to maintain and cost effective. These advantages and others are described in more detail in the following detailed description.

SUMMARY OF THE INVENTION

The present invention is defined in the independent claims. Preferred variants are defined in the independent claims. In particular, the present invention relates to an oven for the elimination of harmful organisms presenting phytosanitary risks present in materials of plant origin in the form of particles, said oven comprising, (a) an enclosure comprising an essentially cylindrical wall extending along a vertical axis, Z, (b) a first circular plate mounted on the wall of said enclosure substantially normal to the vertical axis, Z, and arranged to rotate at a first speed of rotation, $v_1$, in a first direction about the vertical axis, Z, the surface of said plate being perforated, and permeable to air, to water vapor and to water, (c) a second circular plate mounted at a certain distance from the first plate on the wall of said enclosure substantially normal to the vertical axis, Z, and arranged to revolve at a second speed of rotation, $v_2$, about said vertical axis, Z, preferably in the reverse direction of rotation to the first plate, the surface of said plate being perforated and permeable to air, to water vapor and to water, (d) a first distribution means for distributing said particles capable of distributing said particles before baking along a radius of the first plate, (e) a first recovery means for recovering the particles distributed on the first plate after a rotation by a given angle thereof, said first recovery means being situated downstream of, and preferably adjacent to, the first distribution means, (f) a transfer means for transferring the particles collected from the first plate by the first recovery means to a second distribution means capable of distributing said particles along a radius of the second plate, and (g) a gas blowing means forming a closed gas cycle, comprising:

a blower for imparting a velocity on a gas flow and directing it toward, a heating station to form a hot gas flow having an initial temperature, $T_0$, and an initial relative humidity, $RH_0$, and then directing it toward, an upstream baffle, deflecting the hot gas flow as a flow substantially parallel to the axis Z, having a first temperature, $T_1$, and a first relative humidity, $RH_1$, passing first of all through the perforated surface of the first plate, where it loses calorific energy and from where a cooled gas flow emerges having a second temperature, T2, and a second relative humidity, RH2, to then pass directly afterward through the perforated surface of the second plate, where it loses more calorific energy and from where a cold gas flow emerges having a third temperature, T3, and a third relative humidity, RH3, to then reach, a downstream baffle deflecting the cold gas flow toward the blower and recommence the gas cycle.

In a first variant of the invention, the first plate is situated above the second plate and the hot gas circulates from top to bottom and is preferably hot air. In a second variant of the invention, the first plate is situated below the second plate and the hot gas circulates from bottom to top and is also preferably hot air.

The oven can comprise a controller configured to check that the first speed of rotation, v1, of the first plate is preferably greater than the second speed of rotation, v2, of the second plate. For example, v2=1/k·v1, wherein, |k|≥1, and the absolute value of k is preferably between 1 and 5, preferably between 2 and 4, more preferably, |k|=3, and wherein v2 is preferably between 0.5 and 1.2 revolutions per hour.

The oven can comprise a controller configured to control the temperatures and relative humidities of the gas flows. In order to effectively eliminate the phytosanitary pests, the first temperature, T1, of the hot gas flow (52) is preferably between 75 and 120° C., preferably between 85 and 100° C., more preferably between 90 and 95° C. The first relative humidity, RH1, of said hot gas flow is preferably between 15 and 60%, preferably 20%. The second temperature, T2, of the cooled gas flow is preferably between 60 and 80° C., preferably between 65 and 70° C., with a value of the second relative humidity, RH2, of said cooled gas flow preferably between 60 and 90%, preferably between 75 and 85%. The third temperature, T3, of the cold gas flow is preferably between 55 and 65° C., preferably between 58 and 62° C., and the third relative humidity, RH3, of said cooled gas flow is preferably between 80 and 100%, preferably between 95 and 99%.

For greater flexibility in the nature of the materials to be treated, the first and second plates preferably comprise a self-supporting rigid structure with high permeability of grating type, on which is placed a filtering layer comprising openings of a size and density corresponding to the permeability desired according to the type and size of the particles to be treated. The maintenance of the plates is also facilitated, with the possibility of changing the filtering layer when it is damaged or clogged.

The first and second distribution means for distributing the particles on the first and second plates, respectively, preferably each comprise at least one Archimedes screw extending along a radius of the first and second plates, respectively, said at least one Archimedes screw being enclosed in an enclosure provided with one or more openings extending along said radius of the plates.

The recovery means of the first plate also preferably comprises at least one Archimedes screw extending along a radius of said plate which is enclosed in an enclosure provided with one or more openings extending along said radius of the first plate. The openings are linked to a scraper or brush capable of collecting and directing the particles brought by the rotation of the plate to the Archimedes screw. In a preferred variant, the oven further comprises a second recovery means for recovering the particles distributed on the second plate after a rotation by a given angle thereof, said second recovery means being situated downstream of, preferably adjacent to, the second distribution means, said recovery means making it possible to recover the particles on the second plate and to transfer them out of the enclosure. The second recovery means of the second plate comprises, for example, at least one Archimedes screw extending along a radius of said plate which is enclosed in an enclosure provided with one or more openings extending along said radius of the second plate, said openings being linked to a scraper or brush capable of collecting and directing the particles brought by the rotation of the plate to the Archimedes screw.

The vertical axis, Z, is preferably centered on the heating duct which forms an essentially cylindrical hollow central enclosure whose wall extends at least from the first plate to the second plate. The central enclosure can thus contain the blower and the heating station.

The oven can comprise a static floor situated below the lower plate situated lowest on said vertical axis, Z. The floor comprises an opening for discharging the finest particles which would be deposited on the floor. The oven can also comprise a scraper fixed securely to the lower plate situated lowest and capable of following the rotational movement thereof to push the particles deposited on the floor toward said discharge opening.

In order to automate the treatment, the first distribution means for distributing said particles on the first plate can be linked upstream to a source of said particles, preferably a silo. The particles preferably comprise waste or byproducts:
  of wood from sawmills or of construction material wood;
  or
  of paper or cardboard.

Said waste or byproducts can be in the form of powder, sawdust, flakes, chips, wafers, pellets, cakes, and/or the particles preferably have a largest average size of between 1 and 150 mm, preferably between 5 and 50 mm.

The present invention relates also to a method for treating organic particles of plant origin for the elimination of harmful organisms presenting phytosanitary risks. The method of the present invention comprises the use of an oven as described above to perform the following steps:

(a) forming a hot gas flow by blowing, using the blower of said oven, a cold gas through the heating station of the oven, and directing the hot gas flow thus formed at a first temperature, T1, and a first relative humidity, RH1, as a flow substantially parallel to the axis Z, passing first of all through the first plate before passing directly afterward through the second plate;

(b) distributing the particles to be treated on the first circular plate passed through first by the hot gas flow and rotating the first plate about the vertical axis, Z, at the first speed of rotation, v1, in order for the particles (20a) distributed on the first plate to reach a treatment temperature, Tt, after a rotation by a given first angle, θ, (c) after rotation of the first plate by a given angle, θ, recovering the particles having the treatment temperature, Tt, from said first plate and transferring them to and distributing on, (d) the second circular plate which is passed through by a cooled gas flow having a second temperature, T2 Tt, and a second relative humidity, RH2, after having passed through the first plate, and rotating the second plate about the vertical axis, Z, at the second speed of rotation, v2, in order to keep the particles at the treatment temperature, Tt, for a time, t1, (e) after rotation of the second plate by a given second angle, θ, recovering the particles having the treatment temperature, Tt, from said second plate and transferring them out of the oven, and (f) directing the cold gas flow having a third temperature, T3<T2, and a third relative humidity, RH3>RH2, after having passed through the second plate to the blower and repeating the steps (a) to (f).

BRIEF DESCRIPTION OF THE FIGURES

For a better understanding of the nature of the present invention, reference is made to the following figures.

DETAILED DESCRIPTION

Figure 1:
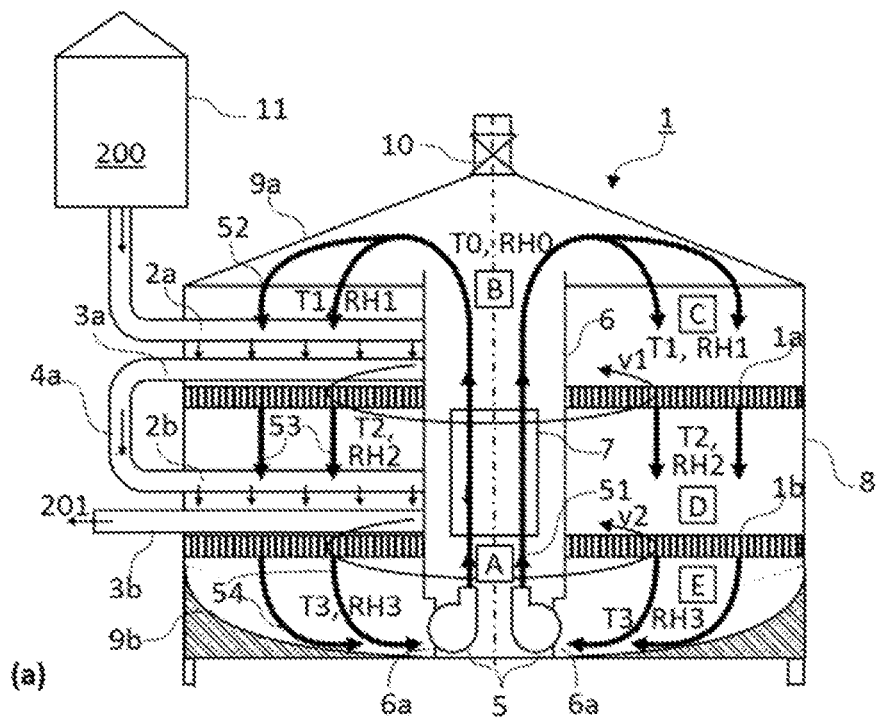
FIG. 1: schematically illustrates two variant ovens according to the present invention.
Figure 1:
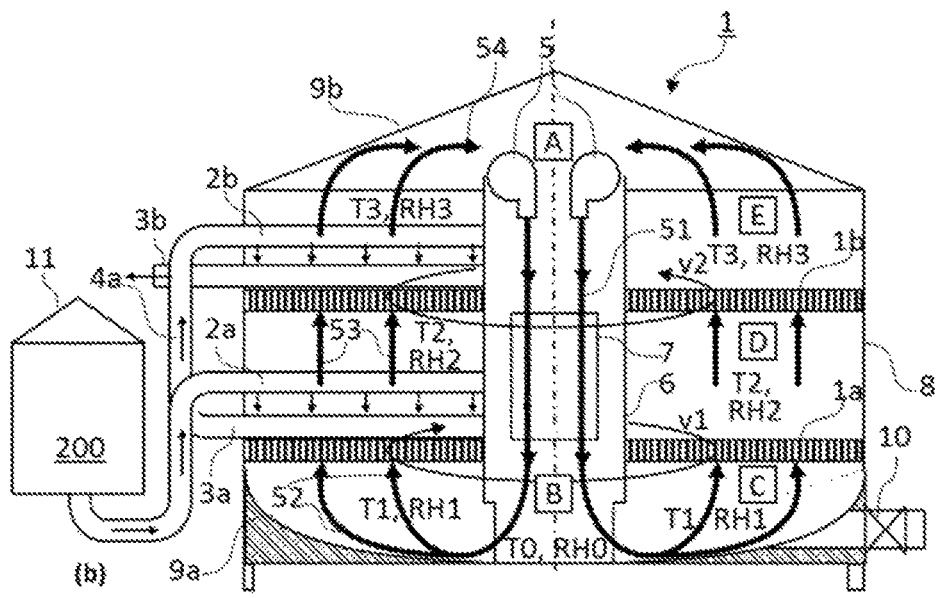

As illustrated in FIG. 1, an oven according to the present invention is defined by an enclosure (8) comprising an essentially cylindrical wall extending a vertical axis, Z. A first circular plate (1a), whose surface is perforated and permeable to air, to water vapor and to water, is mounted on the wall of said enclosure (8) substantially normal to the vertical axis, Z. The first plate is arranged to rotate at a first speed of rotation, v1, in a first direction about the vertical axis, Z.

A second circular plate (1b), whose surface is perforated and permeable to air, to water vapor and to water, is mounted at a certain distance from the first plate on the wall of said enclosure (8) substantially normal to the vertical axis, Z. The second plate is arranged to revolve at a second speed of rotation, v2, about said vertical axis, Z. The directions of rotation of the first and second plates can be identical or reversed. Preferably, the direction of rotation of the second plate is the reverse of that of the first plate. The second speed of rotation, v2, is preferably less than or equal to the first speed of rotation, v1: v1=k v2 (or v2=1/k v1), with k≥1. Such a difference in speeds of rotation makes it possible, on the one hand, for the particles (20a) located on the first plate to reach the treatment temperature, Tt, after a rotation of the first plate and, on the other hand, for the particles (20b) located on the second plate to maintain the treatment temperature, Tt, for the treatment time, t1, during a rotation of the second plate.

A first distribution means (2a) for distributing said particles is arranged above the first plate, preferably extending along a radius of said first plate. The first distribution means makes it possible to distribute said particles (200) to be treated, before baking, along a radius of the first plate (1a). A first recovery means (3a) is arranged downstream of the first distribution means (2a). It makes it possible to recover the particles distributed on the first plate (1a) after a rotation by a given angle thereof. The given angle is as close as possible to 360° C.; it is for example from 340 to 359° C. In this case, said first recovery means extends preferably along a radius of the first plate and is adjacent to the first distribution means (2a). As indicated in FIG. 2(b), the angle of rotation, θ, of a plate is measured from the corresponding distribution means.

A transfer means (4a) making it possible to transfer, to a second distribution means (2b), particles (20t) collected from the first plate (1a) by the first recovery means (3a). The second recovery means (2b) is intended to distribute said particles along a radius of the second plate (1b). The terms "upstream" and "downstream" are defined here with respect to the direction of movement of the particles or of the gas, depending on the case.

The second distribution means (2b) extends preferably along a radius of said second plate. In a preferred variant of the invention, the second plate (1b) also comprises a recovery means (3b) for recovering particles deposited on the second plate after a rotation by a given angle thereof. As for the recovery means (3a) of the first plate discussed above, the second recovery means is situated downstream of the second distribution means (2b). In order to maximize the angle of rotation, the second recovery means extends preferably along a radius of the second plate and is adjacent to the second distribution means.

The oven of the present invention also comprises a gas blowing means forming a closed gas cycle. As illustrated in FIGS. 1 & 2(a), the gas blowing means comprises: a blower (5), for example comprising one or more fans, for imparting a velocity on a gas flow (51) and directing it toward a heating station (7) to form a hot gas flow (52) having an initial temperature, T0, and an initial relative humidity, RH0. The heating can be situated in a heating duct (6) centered on the vertical axis Z forming an essentially cylindrical hollow central enclosure whose wall extends at least from the first plate (1a) to the second plate (1b), as illustrated in FIG. 1. Alternatively, the heating station can be located outside of the enclosure and benefit from an externally available heat source. After having accumulated calorific energy in the heating station, the hot gas flow is directed to an upstream baffle which deflects the hot gas flow toward the first plate (1a), as a flow substantially parallel to the axis Z. Before reaching the first plate, the gas has a first temperature, T1, equal to or slightly lower than T0, and a first relative humidity, RH1, equal to or slightly greater than RH0, if T1<T0.

The gas then passes first of all through the particles (20a) distributed on the perforated surface of the first plate (1a), where it loses calorific and kinetic energy. The gas emerges from the first plate forming a cooled gas flow (53) having a second temperature, T2, less than T1, and a second relative humidity, RH2, greater than RH1. The cooled gas flow (53) continues its travel to then pass directly afterward through the particles (20b) distributed on the perforated surface of the second plate (1b), where it loses more calorific energy and from where a cold gas flow (54) emerges having a third temperature, T3, less than T2, and a third relative humidity, RH3, greater than RH2. The terms "hot gas", "cooled gas", and "cold gas" are mutually relative terms, such that T1>T2>T3, where T1, T2 and T3 are the temperatures of the "hot", "cooled" and "cold" gases, respectively.

A downstream baffle makes it possible to deflect the cooled gas flow toward the blower and recommence the gas cycle. Unlike a drier, the objective of the oven of the present invention is not to drain moisture from the particles but to raise the particles to a temperature, Tt, and to maintain them at that temperature for a time, t1. For this reason, even if the gas is charged with moisture during a first cycle, there is no need to evacuate it or to dry it for the next cycle. On the contrary, since water is a good heat conductor, a certain moisture content helps to speed up the heat transfer from the gas to the particles. Unlike a drier, an oven according to the present invention therefore preferably operates with a closed gas cycle. A valve (10) is however advantageously arranged in order to allow at least part of the gas to be evacuated from a cycle and to be replaced by a fresh gas, if that were to prove necessary.

The first and second plates (1a, 1b) are preferably composed of a self-supporting rigid structure with high permeability of grating type. A filtering layer comprising openings of a size and density corresponding to the permeability desired according to the type and size of the particles to be treated can then be placed directly on the rigid structure. Thus, one and the same oven can be used to treat particles of very different sizes, simply by changing the filtering layer. The latter can be a perforated plate, a mat, a grating or a fabric woven from plant fibers (for example, hemp, cotton), synthetic fibers (for example, polyethylene, polypropylene, polyester), or metal fibers (for example, steel). Alternatively, the filtering layer can be formed by a tarpaulin perforated with holes of size and density suited to the particles to be treated.

Particles of plant origin according to the present invention comprise, for example, particles of wood, of bark, of cones. They can take the form of wood wool, pellets, chips, sawdust, fibers, powders, wafers, cakes, etc. The particles can have a largest average size of between 1 and 150 mm, preferably between 5 and 50 mm, in which the "largest size" is the distance separating the points of a particle furthest away from one another. The particles can for example be waste or byproducts of wood from sawmills or of construction material wood, or even of paper or of cardboard. The particles can advantageously be stored in a silo (11) or any other storage container, linked directly to the first distribution means (2a) thus making it possible to distribute the particles directly from their place of storage onto the first plate.

The purpose of the first distribution means (2a) for distributing the particles to be treated on the first plate (1a) is to distribute the particles to be heated uniformly along a radius of the first plate. Generally, the first distribution means (2a) therefore comprises:
- a structure extending from the outer periphery to the inner periphery of the first plate, preferably, but not necessarily, along a radius thereof,
- means for transporting the particles from the outer periphery to the inner periphery of the first plate, and finally
- means for depositing said particles from the transport means to the first plate.

Several solutions are possible. For example, the transporting of the particles from the outer periphery to the center of the first plate can be ensured by a conveyor belt, either perforated, or inclined transversely so as to allow the particles to sprinkle onto the plate situated below. To assist in the sprinkling, the belt can be vibrated. In an alternative and preferred variant illustrated in FIG. 2(b), the first distribution means (2a) comprises at least one Archimedes screw extending along a radius of the first plate (1a), in order to transport the particles from the periphery to the inner periphery of the corresponding plate. Said at least one Archimedes screw is enclosed in an enclosure provided with one or more openings extending downward and along said radius of the first plate (1a) in order to allow the sprinkling of the particles on said plate.

Figure 2:
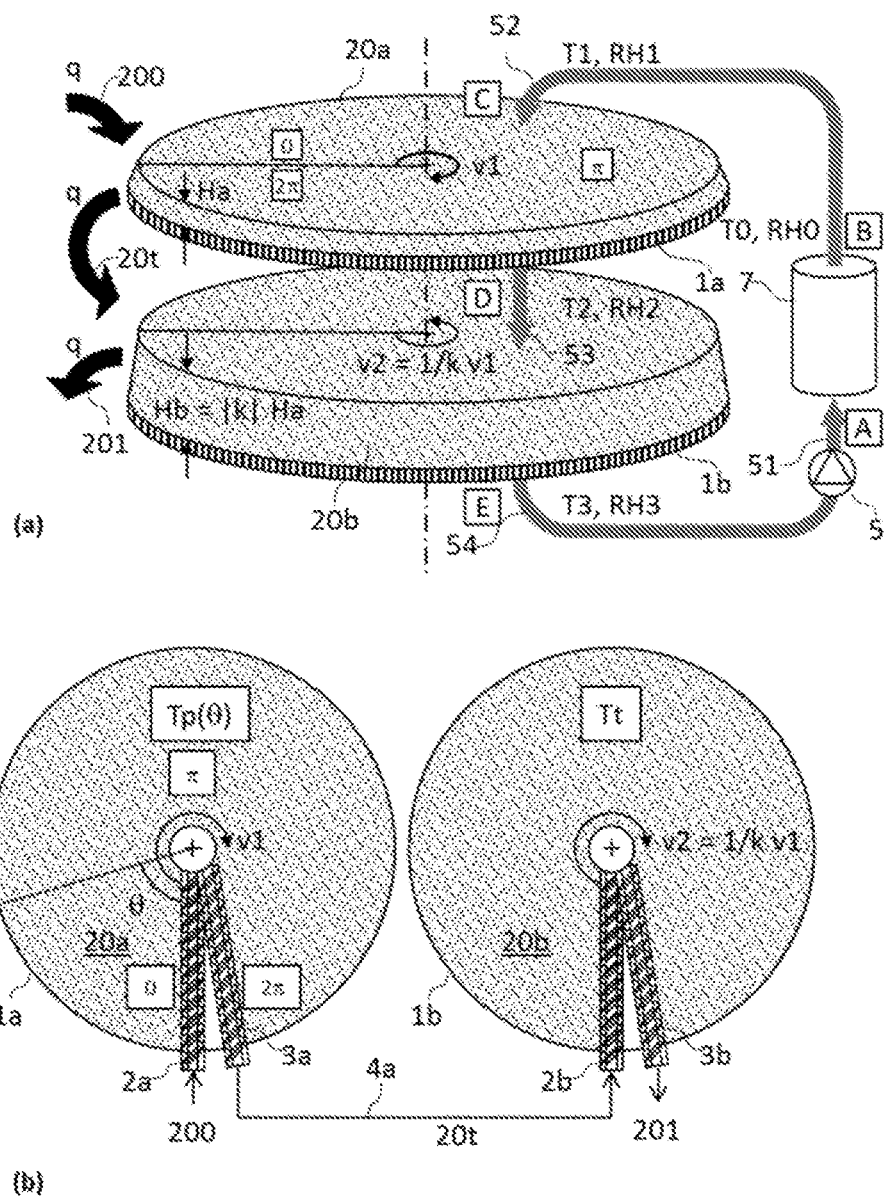
FIG. 2: illustrates (a) the flows of particles and of gas through the plates of the oven of the present invention and (b) a plan view of the plates with indication of the flows of particles.
Figure 3:
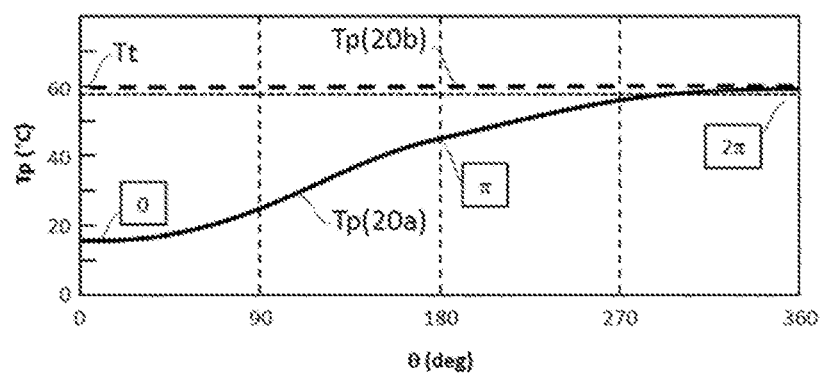
FIG. 3: illustrates the temperature, Tp, of the particles according to their angular position on the first and second plates, respectively.

The particles therefore accumulate on a radius of the first plate with an angle of rotation θ of 0° (see $0$ in FIGS. 2 & 3). Since the first plate revolves at a speed, v1, about the axis Z, a uniform layer of particles (20a) of height Ha, covers the surface of the first plate. As illustrated in FIG. 3, during the rotation of the first plate, the particles are heated by the hot gas flow (52) and their temperature, Tp, increases with the angle of rotation, θ, of the first plate (Tp=Tp(θ)). The speed of rotation, v1, of the first plate is defined in order to ensure that the particles (20a) reach the treatment temperature, Tt, after the first plate has revolved by a given angle, less than or equal to, and as close as possible to 360° (see $2\pi$ in FIGS. 2 & 3). The speed of rotation, v1, therefore depends on the type and the properties of the bed of particles and on the characteristics of the hot gas flow (52), including its temperature, T1, its relative humidity, RH1, and its flow rate. The treatment temperature, Tt, is preferably between 55 and 80° C., preferably Tt≥60° C.

At this point, the particles (20a) are collected at a temperature ≥Tt by the recovery means (3a) to be transferred to the second plate (1b). As illustrated in FIG. 2(b), the recovery means (3a) of the first plate (1a) preferably comprises at least one Archimedes screw extending along a radius of said plate which is enclosed in an enclosure provided with one or more openings extending along said radius of the corresponding plate. The openings are linked to a scraper or brush capable of collecting and directing the particles brought by the rotation of the plate to the Archimedes screw. The type of transfer means (4a) for transferring the particles from the first plate (1a) to the second plate (1b) depends on the configuration of the oven. If the first plate (1a) is the upper plate, the transfer means can be a simple tube linking the recovery means (3a) of the first plate to the distribution means (2b) of the second plate, in which the particles drop by gravity. If, on the other hand, the first plate is the lower plate, it is preferable for the transfer means (4a) to comprise an Archimedes screw making it possible to raise the particles from the lower first plate to the higher second plate.

The particles (20t) are thus transferred to a second distribution means (2b) which distributes the particles uniformly on the surface of the second plate (1b). The second distribution means can be of the same type as the first distribution means discussed above. Generally, but not necessarily, the first and second distribution means are identical. As illustrated in FIG. 2(b), the second distribution means (2b) preferably comprises at least one Archimedes screw extending along a radius of the second plate (1b). The at least one Archimedes screw is enclosed in an enclosure provided with one or more openings extending along said radius of the plate (1b). The particles therefore accumulate on a radius of the second plate with an angle of rotation θ of 0°.

Since the second plate revolves at a speed, v2, about the axis Z, a uniform layer of particles (20b) of height Hb, covers the surface of the second plate. The speed of rotation, v2, of the second plate is generally different from the speed of rotation, v1, of the first plate. In effect, if the speed of rotation, v1, is optimized for the particles (20a) to reach the treatment temperature, Tt, after a revolution of the first plate (that is to say after a rotation of the particles from the first distribution means (2a) to the recovery means (3a)), the speed of rotation, v2, of the second plate depends on the time, t1, that the particles have to remain at the temperature, Tt. For example, if a heat treatment is taken as defined in ISPM 15 standard imposing a treatment at a treatment temperature, Tt, of at least 56° C. for a time, t1, of 30 minutes, the speed of rotation, v2, of the second plate will be approximately equal to v2≅360 degrees/30 min=12 degrees/min. As illustrated in FIG. 3, during the rotation of the second plate, the particles are maintained by the cooled gas flow (53) at their treatment temperature, Tt, throughout the rotation of the second plate.

The speed of rotation, v1, of the first plate can be expressed as a function of the speed of rotation, v2, of the second plate as: v1=k v2. If the first and second plates revolve in reverse directions, k will be negative. In most cases, the time of exposure to the hot gas flow (52) of the particles (20a) placed on the first plate required to heat them to a treatment temperature, Tt, is less than the time, t1, for which the particles (20b) have to remain at the treatment temperature, Tt. If the speed of rotation, v1, of the first plate is greater than or equal to the speed, v2, of the second plate, the absolute value of k is then greater than or equal to 1 (|v1|≥|v2|⇔|k|≥1). For example, if v2 is between 0.5 and 1.2 revolutions per hour, the absolute value of k can be between 1 and 5, preferably between 2 and 4, and more preferably, |k|=3±0.5.

Through the principle of conservation of mass, the thicknesses, Ha and Hb, of the layers of particles (20a, 20b) located on the first and second plates (1a, 1b) depend directly on the flow rates, q, of distribution of the particles on the respective plates, and on the speeds of rotation. The particles to be treated (200) are distributed on the first plate at a flow rate, q [kg/s]. The first plate revolves at a speed, v1, for a revolution before recovering the particles (20a) and transferring them to the second plate. There, they are distributed on the second plate at the same flow rate, q, as for the first plate (see FIG. 2(a)). The second plate revolves at a speed, v2, for a revolution before recovering the particles (20b) and discharging the particles (201) at the same flow rate, q, as previously defined. Since the flow rates, q, of the particles (200), (20t) and (201) are equal, the heights Ha and Hb can be expressed as, Hb=|k| Ha.

Figure 4:
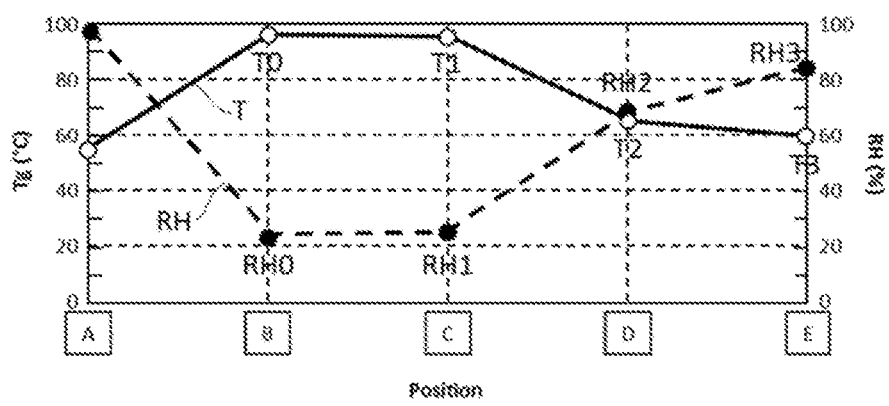
FIG. 4: illustrates the temperature, Tg, and the relative humidity, RH, of the gas at different positions in the oven.

The hot gas, for example hot air or any other gas for example from a combustion method, follows a path in the same direction as that of the particles, i.e. passing first of all through the first plate to heat the particles (20a) to the treatment temperature, Tt, then through the second plate to keep them at said treatment temperature, Tt, for a time, t1. On the graph of FIG. 4, the gas flow (51) leaving a blower (5) has a given temperature, Tg, and relative humidity, RH (see position A in FIGS. 1, 2 and 4). At this stage, the gas, for example air, is at its lowest temperature. For example, the temperature of the gas flow (51) is of the order of 55° C. The dew point of the air dependent on the temperature, the relative humidity, RH, of the gas flow (51) is highest. For example, RH=100%. The gas flow passes through a heating station (7) in order to increase the temperature thereof to a value, T0, which has the effect of lowering the value of the relative humidity, RH0 (see position B in FIGS. 1, 2 and 4). For example, the temperature, T0, of the hot gas flow can be between 75 and 120° C., preferably between 85 and 100° C., or preferably between 90 and 95° C. The relative humidity, RH0, of said hot gas flow can be between 15 and 60%, preferably between 30 and 40%.

At the output of the heating station, the heated gas flow is deflected to be oriented parallel to the axis Z, to be directed toward the first plate. The first temperature, T1, and the first relative humidity, RH1, of the gas flow (52) are substantially identical to T0 and RH0, differing only by the lowering of the temperature, T1 relative to T0, by effects of losses (poor insulation, etc.) (see position C in FIGS. 1, 2 and 4). As for T0, the first temperature T1, of the hot gas flow (52) can be between 75 and 120° C., preferably between 85 and 100° C., more preferably between 90 and 95° C., and the first relative humidity, RH1, of said hot gas flow can be between 15 and 60%, preferably RH1≥20%. In passing through the bed of particles (20a) and the first plate, the gas flow (52) transfers a part of its energy and the particles (20a) are heated as a function of the time of exposure to the gas flow, and therefore as a function of the position, θ, on the first plate (Tp=Tp(θ), see FIG. 3, #Tp(20a)).

The cooled gas flow (53), after having passed through the first plate, is therefore cooled to a second temperature, T2<T1. It therefore loses calorific energy, but also a part of its kinetic energy in passing through the bed of particles (20a) and the perforated surface of the first plate (1a). The relative humidity therefore increases to a second value, RH2>RH1 (see position D in FIGS. 1, 2 and 4). For example, the second temperature, T2, of the cooled gas flow is between 60 and 80° C., preferably between 65 and 70° C., and the second relative humidity, RH2, of said cooled gas flow is between 60 and 90%, preferably between 75 and 85%.

The cold gas flow (54), after having passed through the second plate, is therefore cooled to a third temperature, T3<T2<T1. It therefore loses calorific energy, but also a part of its kinetic energy in passing through the bed of particles (20b) and the perforated surface of the second plate (1b). The relative humidity therefore increases to a third value, RH3>RH2>RH1 (see position E in FIGS. 1, 2 and 4). For example, the third temperature T3, of the cold gas flow is between 55 and 65° C., preferably between 58 and 62° C., and the third relative humidity, RH3, of said cold gas flow is between 80 and 100%, preferably between 95 and 99%. The gas used to treat the particles can be any type of gas that does not present any danger of explosion or of toxicity or of pollution. The gas can preferably be air.

Figure 5A:
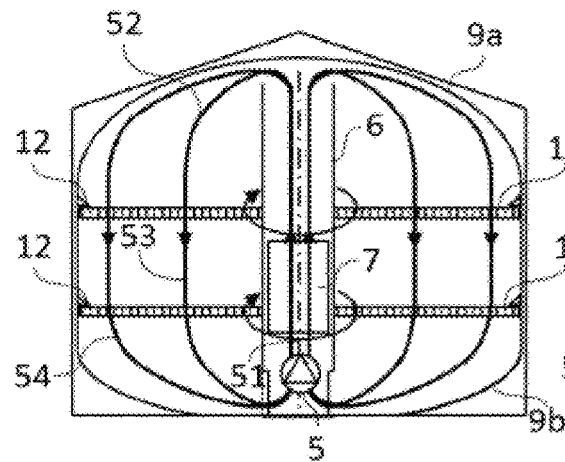
FIG. 5: illustrates different geometries of upstream and downstream baffles.
Figure 5B:
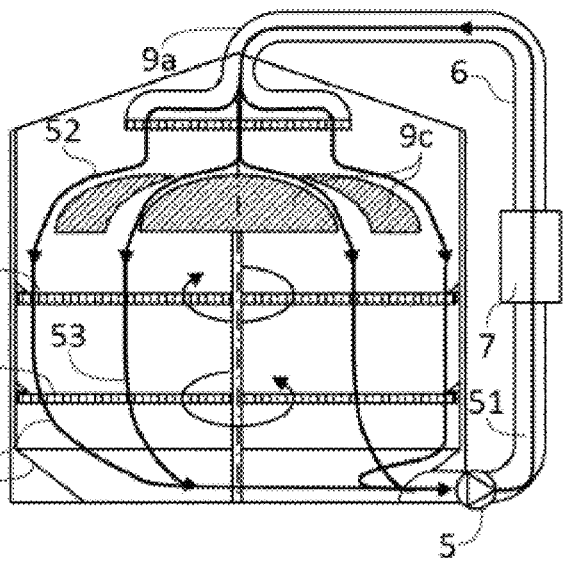

In a first variant of the invention, illustrated in FIGS. 1(a), 2(a) and 5, the first plate (1a) is situated above the second plate (1b). The hot gas then circulates from top to bottom. This variant has the advantage of blowing the particles against the surfaces of the plates, making it possible to reduce dust in suspension. However, the beds of particles arranged on the first and second plates are thus made denser, reducing their permeability to the gases and making it more difficult to individually heat up the particles. This variant is therefore preferred for treating very light or fine particles or, on the contrary, fairly large particles, forming a bed of high permeability to the gases, even if compressed.

Figure 6A:
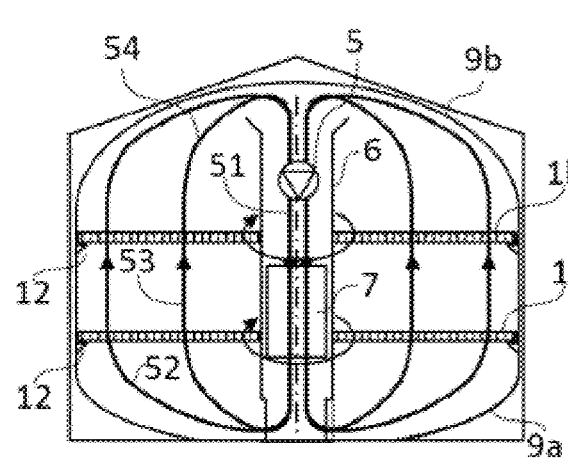
FIG. 6: illustrates different geometries of upstream and downstream baffles.
Figure 6B:
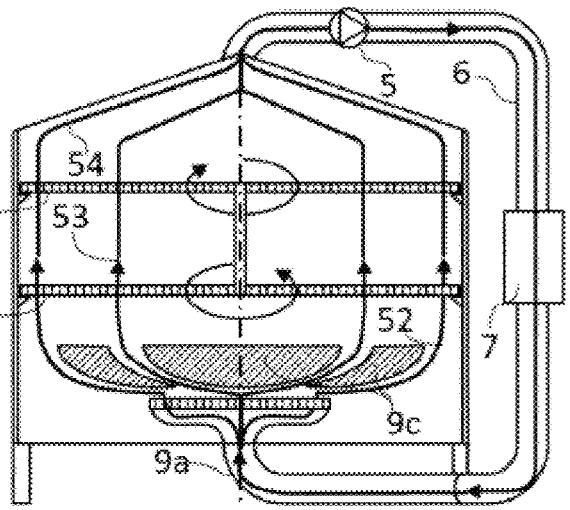

In a second variant of the present invention, illustrated in FIGS. 1(b)&6, the first plate (1a) is situated below the second plate (1b). The hot gas then circulates from bottom to top. If the particles are very light, a cloud in suspension can be formed which is to be avoided. By contrast, if the particles have a suitable weight, such a variant is advantageous in that a fluidized bed can thus be formed, which allows the hot gas to reach practically each particle individually, thus increasing the effectiveness of the heat transfer to the particles. The choice of one or other of the variants regarding the relative position of the first and second plates therefore depends on the nature of the particles to be treated and on the gas flows used.

The upstream and downstream baffles (9a, 9b) do not need to have a particular geometry provided that they make it possible to change the orientation of the gas flow. For example, in the case of a cylindrical enclosure (8), a roof, for example flat or conical, and a horizontal floor can form the upstream and downstream baffles. In effect, whatever the orientation of the hot gas flow (52) entering into the enclosure upstream of the first plate (1*a*), it will necessarily be deflected toward the perforated surface of the first plate by the roof or the floor, depending on where the first plate is located, thus serving as upstream baffle (9*a*). Likewise, the cold gas flow (54) downstream of the second plate is necessarily deflected toward the blower by the floor or roof, depending on the position of the second plate, thus serving as downstream baffle (9*b*).

The upstream and downstream baffles (9*a*, 9*b*) can preferably have a profiled geometry making it possible to deflect the hot (52) and cold (54) gas flow by reducing the turbulences and smoothing the flows in laminar or almost laminar fashion. Thus, as illustrated in FIGS. 5&6, the upstream baffle (9*a*) makes it possible to orient the hot gas (52) substantially normal to the surface of the first plate. As illustrated in FIGS. 5(*a*)&6(*a*), if the heating duct (6) forms an essentially cylindrical hollow enclosure centered on the vertical axis, Z, the upstream baffle (9*a*) can be formed by an arch in the ceiling or on the floor of the enclosure, depending on whether the first plate (1*a*) is located above or below the second plate, respectively. The arch can be a curve as illustrated in FIGS. 5(*a*)&6(*a*) or conical. As illustrated in FIGS. 5(*b*)&6(*b*), in the case of a heating duct (6) situated outside of the enclosure of the oven, said heating duct comprises a bend (9*a*) making it possible to deflect the gas flow in the direction normal to the first plate. The heating duct can be provided at its downstream end with a distribution knob provided with a grating. An upstream distributor (9*c*) can be situated downstream of the downstream end of the heating duct to ensure that the hot gas (52) is distributed over all of the surface of the first plate.

In order to prevent the hot gas from short-circuiting the particles placed on the plates and passing through the periphery of the plates, between the circumference of a plate and the enclosure of the oven, means (12) for sufficiently sealing the circumference of the plates are provided. For example, a skirt can extend from the enclosure of the oven and overlap a part of the upstream surface of each plate over their circumference (see FIGS. 5&6). The plates can also be fitted into a groove provided on the inner surface of the enclosure of the oven. Any other dynamic sealing means known to the person skilled in the art can be used without modifying the present invention.

The downstream baffles make it possible to deflect the cold gas (54) after having passed through the second plate (1*b*) toward the fan or fans forming the blower (5) or compressor which gives back to the cold gas stream kinetic energy before sending it to the heating station (7) in the heating duct (6). In the case of a heating duct (6) centered on the vertical axis Z, as illustrated in FIGS. 5(*a*)&6(*a*), the downstream baffles (9*b*) make it possible to redirect the cold gas flow (54) toward openings distributed over the periphery of the heating duct, to the blower making it possible to give back kinetic energy to the cold gas flow and to redirect it to the heating station to give calorific energy back to it. In the case of an external heating duct (6) as illustrated in FIGS. 5(*b*)&6(*b*), the downstream baffles (9*b*) make it possible to direct the cold air flow (54) toward an orifice situated in the wall of the enclosure or in the roof of the oven giving access to the heating duct. The downstream baffles (9*b*) can be formed by a surface with double curvature, or conical, or be formed by planar surfaces distributed over the circumference of the enclosure of the oven downstream of the second plate.

The figures illustrate ovens comprising two plates. However, to reduce the footprint occupied by the equipment, it is perfectly possible to mount:

at least one third circular plate mounted substantially horizontally at a certain distance, and separated from the first plate (1*a*) by, the second plate (1*b*), in rotation about said vertical axis, Z, the surface of said plate being perforated and permeable to air, to water vapor and to water, and a transfer means for transferring the particles collected from the second plate (1*b*) by the recovery means (3*b*) to a third distribution means capable of distributing said particles along a radius of the third plate.

With a view to the distribution of the granule size analysis of the particles of one and the same type, it is difficult to avoid having the finest fraction of the particles passing through the perforations of the plates and falling on the lower plates, then onto the floor of the enclosure of the oven enclosing the plates. In order to avoid too great an accumulation of particles on the floor and also to recover them, it is advantageous to provide the floor with an opening for discharging the finest particles would be deposited on the floor. Furthermore, a scraper or brush fixed securely to the lower plate and capable of following the rotational movement thereof is used to push the particles deposited onto the floor toward said discharge opening. Since the scraper or brush is fixed to the lower plate, there is no need for it to be individually motorized.

The present invention relates also to a method for treating organic particles of plant origin for the elimination of harmful organisms presenting phytosanitary risks. The method of the present invention uses an oven as discussed above and comprises the following steps, (a) forming a hot gas flow (52) by blowing, using the blower (5) of said oven (1), a cold gas (51) through the heating station (7) of the oven, and directing the hot gas flow (52) thus formed at a first temperature, T1, and a first relative humidity, RH1, as a flow substantially parallel to the axis Z, passing first of all through the first plate (1*a*) before directly afterward through the second plate (1*b*);

(b) distributing the particles (200) to be treated on the first circular plate (1*a*) passed through first by the hot gas flow (52) and rotating the first plate about the vertical axis, Z, at the first speed of rotation, v1, in order for the particles (20*a*) distributed on the first plate to reach a treatment temperature, Tt, after a rotation by a given first angle, θ, (c) after rotation of the first plate by a given angle, θ, recovering the particles having the treatment temperature, Tt, from said first plate and transferring them to and distributing on, (d) the second circular plate (1*b*) which is passed through by a cooled gas flow (53) having a second temperature, T2 Tt, and a second relative humidity, RH2, after having passed through the first plate, and revolving the second plate about the vertical axis, Z, at the second speed of rotation, v2, in order to keep the particles at the treatment temperature, Tt, for a time, t1, (e) after rotation of the second plate by a given second angle, θ, recovering the particles (20*b*) having the treatment temperature, Tt, from said second plate and transferring them out of the oven, and (f) directing the cold gas flow (54) having a third temperature, T3<T2, and a third relative humidity, RH3>RH2, after having passed through the second plate to the blower and repeating the steps (a) to (f).

The oven of the present invention makes it possible to continuously treat, according to the international standards, organic particles of plant origin of very different sizes and natures for the elimination of harmful organisms that present phytosanitary risks. The energy required for the treatment is optimized by separating the steps of heat to a treatment temperature, Tt, on the first plate and of keeping the particles at this temperature, Tt, for a treatment time, t1, on a second plate. The oven is simple and economical to build, easy to maintain and ensures a reproducibility and constancy of the treatment applied to the particles.

| REF | DEFINITION |
|---|---|
| 1 | oven |
| 1a | first plate |
| 1b | second plate |
| 2a | first distribution means |
| 2b | second distribution means |
| 3a | first recovery means |
| 3b | second recovery means |
| 4a | first transfer means |
| 5 | blower |
| 6 | heating duct |
| 6a | inlet window into the heating duct |
| 7 | heating station |
| 8 | enclosure of the oven |
| 9a | upstream baffle |
| 9b | downstream baffle |
| 9c | upstream distributor |
| 10 | chimney provided with a valve |
| 11 | silo |
| 12 | means for sealing the circumference of the plates |
| 20a | particles located on the first plate |
| 20b | particles located on the second plate |
| 20t | particles being transferred from the first plate to the second plate |
| 51 | gas flow leaving the blower |
| 52 | hot gas flow leaving the heating station |
| 53 | hot gas flow having passed through the first plate, but not the second |
| 54 | cooled gas having passed through the second plate |
| 200 | particles to be treated |
| 201 | particles after treatment |
| q | flow rate of particles (kg/s) |
| Ha | height of the bed of particles on the first plate (1a) |
| Hb | height of the bed of particles on the second plate (1b) |
| k | proportionality factor between v1 and v2, $v1 = k\, v2$, $k \geq 1$ |
| RH0 | initial relative humidity of the gas (on leaving the heating station) |
| RH1, 2, 3 | first, second and third relative humidities of the gas |
| t1 | treatment time at the temperature Tt or above |
| T0 | initial temperature of the gas (on leaving the heating station) |
| T1, 2, 3 | first, second and third gas temperatures |
| Tt | particle treatment temperature |
| v1 | speed of rotation of the first plate |
| v2 | speed of rotation of the second plate |
| θ | angle of rotation of a plate from the corresponding distribution means |

The invention claimed is:

1. An oven (1) for the elimination of harmful organisms that present phytosanitary risks present in materials of plant origin in the form of particles, said oven comprising, comprising:
    (a) an enclosure (8) comprising an essentially cylindrical wall extending along a vertical axis, Z;
    (b) a first circular plate (1a) mounted on the wall of said enclosure (8) normal to the vertical axis, Z, and arranged to rotate at a first speed of rotation, v1, in a first direction about the vertical axis, Z, a surface of said first circular plate being perforated, and permeable to air, to water vapor and to water;
    (c) a second circular plate (1b) mounted at a certain distance from the first plate on the wall of said enclosure (8) normal to the vertical axis, Z, and arranged to rotate at a second speed of rotation, v2, about said vertical axis, Z, a surface of said second circular plate being perforated and permeable to air, to water vapor and to water;
    (d) a first distribution means (2a) for distributing said particles capable of distributing said particles before baking along a radius of the first plate (1a)];
    (e) a first recovery means (3a) for recovering the particles (20a) distributed on the first plate (1a) after a rotation by a given angle thereof, said first recovery means being situated downstream of, and preferably adjacent to, the first distribution means (2a);
    (f) a transfer means (4a) for transferring the particles collected from the first plate (1a) by the first recovery means (3a) to a second distribution means (2b) capable of distributing said particles (20t) along a radius of the second plate (1b); and
    (g) a gas blowing means forming a closed gas cycle comprising:
        a blower (5) for imparting a velocity on a flow of gas (51) and directing it toward,
        a heating station (7) to form a hot gas flow (52) having an initial temperature, T0, and an initial relative humidity, RH0, and then directing the hot gas flow (52) toward,
        an upstream baffle, deflecting the hot gas flow as a flow substantially parallel to the axis Z, having a first temperature, T1, and a first relative humidity, RH1, passing first of all through the perforated surface of the first plate (1a), where it loses calorific energy and from where a cooled gas flow (53) emerges having a second temperature, T2, and a second relative humidity, RH2, to then pass directly afterward through the perforated surface of the second plate (1b), where it loses more calorific energy and from where a cold gas flow (54) emerges having a third temperature, T3, and a third relative humidity, RH3, to then reach,
        a downstream baffle deflecting the cold gas flow (54) toward the blower and recommencing the gas cycle.

2. The oven (1) as claimed in claim 1, wherein the first plate (1a) is situated above the second plate (1b) and wherein the hot gas flow circulates from top to bottom and is preferably hot air.

3. The oven (1) as claimed in claim 1, wherein the first plate (1a) is situated below the second plate (1b) and wherein the hot gas flow circulates from bottom to top and is preferably hot air.

4. The oven (1) as claimed in claim 1, further comprising a controller configured to check that the first speed of rotation, v1, of the first plate is greater than the second speed of rotation, v2, of the second plate, with $v2=1/k\cdot v1$, wherein, $|k|\geq 1$.

5. The oven (1) as claimed in claim 1, further comprising a controller configured to check that the first temperature, T1, of the hot gas flow (52) is between 75 and 120° C., and the first relative humidity, RH1, of said hot gas flow is between 15 and 60%.

6. The oven (1) as claimed in claim 1, further comprising a controller configured to check that, the second temperature, T2, of the cooled gas flow (53) is between 60 and 80° C., and the second relative humidity, RH2, of said cooled gas flow is between 60 and 90%, and that, the third temperature, T3, of the cold gas flow (54) is between 55 and 65° C. and the third relative humidity, RH3, of said cooled gas flow is between 80 and 100%.

7. The oven (1) as claimed in claim 1, the first and second plates (1a, 1b) further comprising a self-supporting rigid structure with high permeability of grating type, on which is placed a filtering layer comprising a plurality of openings of a size and density corresponding to the permeability desired according to the type and size of the particles to be treated.

8. The oven (1) as claimed in claim 1, the first and second distribution means (2a, 2b) for distributing the particles on the first and second plates (1a, 1b), respectively, each further comprising at least one Archimedes screw extending along a radius of the first and second plates (1a, 1b), respectively, said at least one Archimedes screw being enclosed in an enclosure provided with one or more openings extending along said radius of the plates (1a, 1b).

9. The oven (1) as claimed in claim 1, the recovery means (3a) of the first plate (1a) further comprising at least one Archimedes screw extending along the radius of said first plate which is enclosed in an enclosure provided with one or more openings extending along said radius of the first plate (1a), said openings being configured for collecting the particles brought by the rotation of the first plate to the Archimedes screw.

10. The oven (1) as claimed in claim 1, further comprising a second recovery means (3b) for recovering the particles distributed on the second plate (1b) after a rotation by a given angle thereof, said second recovery means being situated downstream of the second distribution means (2b), said second recovery means making it possible to recover the particles on the second plate and to transfer them out of the enclosure.

11. The oven (1) as claimed in claim 10, the second recovery means (3b) of the second plate (1b) further comprising at least one Archimedes screw extending along a radius of said second plate which is enclosed in an enclosure provided with one or more openings extending along said radius of the second plate (1b), said openings being configured for collecting the particles brought by the rotation of the second plate to the Archimedes screw.

12. The oven (1) as claimed in claim 1, wherein the vertical axis, Z, is centered on a heating duct (6) which forms an essentially a cylindrical hollow central enclosure whose wall extends at least from the first plate (1a) to the second plate (1b), said enclosure containing the blower and the heating station.

13. The oven (1) as claimed in claim 1, further comprising a static floor situated below whichever of the first plate or the second plate is situated lowest on said vertical axis, Z, said floor comprising an opening for discharging the finest particles which would be deposited on the floor.

14. The oven (1) as claimed in claim 1, wherein the first distribution means (2a) for distributing said particles on the first plate (1a) is linked upstream to a source (11) of said particles, said particles comprising waste or byproducts:

of wood from sawmills or of construction material wood, or of paper or cardboard, wherein said waste or byproducts are in the form of powder, sawdust, flakes, chips, wafers, pellets, cakes, or a combination thereof, and wherein the particles have a largest average size of between 1 and 150 mm.

15. The oven (1) as claimed in claim 1 wherein said second circular plate (1b) rotates in the reverse direction relative to the rotation direction of the first circular plate (1a).

16. The oven (1) as claimed in claim 1 wherein the hot gas flow is hot air.

17. The over (1) as claimed in claim 1 wherein the absolute value of k is between 1 and 5, and wherein v2 is between 0.5 and 1.2 revolutions per hour.

\* \* \* \* \*